United States Patent [19]

Smith

[11] 4,250,881
[45] Feb. 17, 1981

[54] CATHETER INSERTION DEVICE
[75] Inventor: Gordon E. Smith, Sun Prairie, Wis.
[73] Assignee: Quest Medical, Inc., Carrollton, Tex.
[21] Appl. No.: 70,717
[22] Filed: Aug. 29, 1979
[51] Int. Cl.³ ............................................. A61M 5/32
[52] U.S. Cl. .............................. 128/214.4; 128/221; 128/347; 128/DIG. 16
[58] Field of Search .................... 128/214.4, DIG. 16, 128/347, 221

[56] References Cited

U.S. PATENT DOCUMENTS

| | | | |
|---|---|---|---|
| 3,388,703 | 6/1968 | Bowes | 128/221 |
| 3,406,685 | 10/1968 | May | 128/214.4 |
| 3,827,434 | 8/1974 | Thompson | 128/214.4 |

Primary Examiner—Hiram Bernstein
Attorney, Agent, or Firm—Isaksen, Lathrop, Esch, Hart & Clark

[57] ABSTRACT

A catheter insertion device (10) is disclosed which is usable to insert a very flexible catheter (12) formed of a silicone elastomer into the blood vessel of a patient. Catheters of highly flexible material, such as silicone elastomer, are highly desirable for use as such catheters in that they do not initiate a build-up of fibrin in the blood stream as do other, more rigid, catheters. A hub member (18) is slidably received over a needle (14) carrying the catheter (12) and a semi-rigid sleeve (26) extends under the proximal end of the catheter (12) so as to aid in removing the catheter (12) from the needle (14) after the needle (14) has been inserted into the blood stream of the patient.

7 Claims, 7 Drawing Figures

CATHETER INSERTION DEVICE

TECHNICAL FIELD

The present invention relates to catheters in general, and, in particular, to a device for inserting a flexible catheter into the blood stream of a patient.

BACKGROUND OF THE PRIOR ART

The prior art is generally cognizant of methods for inserting catheters into the blood stream of patients involving the insertion of the catheter into the patient while the catheter is carried over a hollow needle, or a trocar. One example of a device utilizing such a method for inserting a catheter into a patient is shown in U.S. Pat. No. 3,714,945, which describes a device suitable for inserting a semi-rigid catheter into the blood stream of the patient. It is generally a problem with all prior art semi-rigid catheter devices, and the apparatus for inserting such catheters, in that the catheters eventually cause a fibrin build-up in the blood vessel into which they are inserted. It has not generally been practicable to introduce more flexible catheters into a blood vessel.

BRIEF SUMMARY OF THE INVENTION

The present invention is summarized in that a catheter insertion device includes an elongated hollow needle sharpened at its distal end, a flexible catheter formed of a silicone elastomer and positioned stretched over the needle, a hub member slidably received over the proximal end of the needle, and a semi-rigid sleeve extending from the hub member toward the distal end of the needle and slidably received around the needle, the proximal end of the catheter being stretched over the sleeve, the sleeve serving to force the catheter off of the needle as the needle is withdrawn through the hub member.

It is an object of the present invention to provide a device suitable for insertion of a highly flexible catheter into the blood vessel of a patient.

It is yet another object of the present invention to provide such a device that will insert a catheter into the blood stream of a patient which will not cause any fibrin build-up within the blood vessel of the patient.

It is yet another object of the present invention to provide such a catheter which can be easily and reliably inserted into the patient.

Other objects, advantages, and features of the present invention will become apparent from the following specification when taken in conjunction with the accompanying drawings.

DETAILED DESCRIPTION OF THE PREFERRED EMBODIMENT

Figure 1:
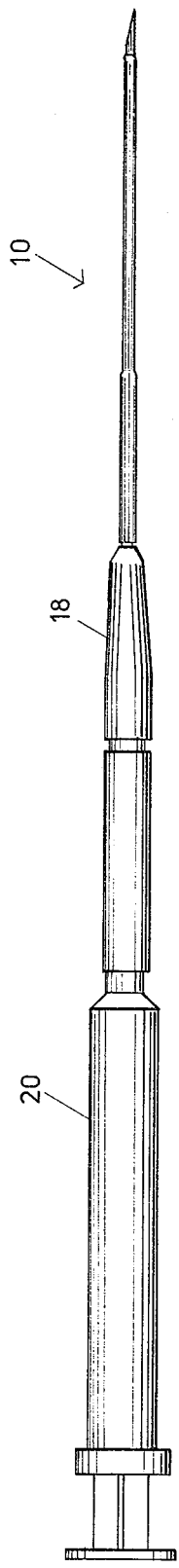
FIG. 1 is a side elevation view of a catheter insertion device constructed in accordance with the present invention.

Shown in FIG. 1 is an infusion catheter insertion device, generally indicated at 10, constructed in accordance with the present invention. The catheter insertion device 10 generally includes a catheter 12 which is initially positioned stretched over an insertion needle 14. At its proximal end, the insertion needle 14 is attached to a needle fitting 16 of a hollow character, and a catheter hub member 18 is positioned around the needle 14 in front of the fitting 16. The hub member 18 is attached to the proximal end of the catheter 12 as will be described below. A hypodermic syringe 20 is shown in FIG. 1 inserted into the needle fitting 16, but it is to be understood that the syringe 20, an optional element, is used only to provide for convenient handling of the remainder of the catheter insertion device 10, and is not itself a part of the device of the present invention.

Figure 2:
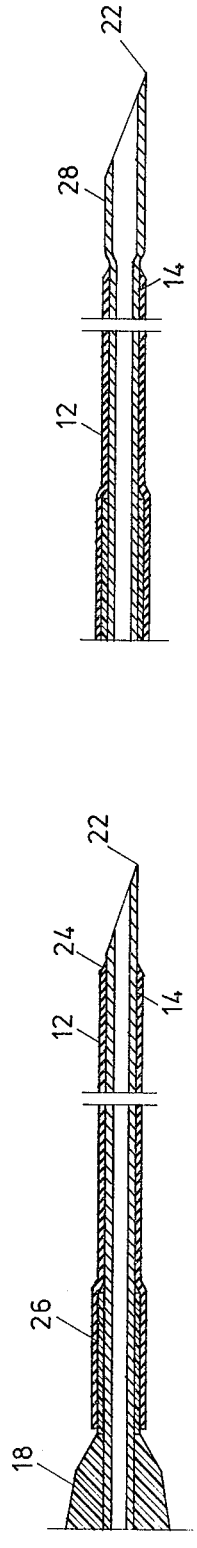
FIG. 2 is a partial cross-sectional view taken along the longitudinal center line of the device of FIG. 1.

As can be seen in the greater detail shown in FIG. 2, the insertion needle 14 is provided at its distal end with a sharpened insertion point 22. From its distal end, the hollow insertion needle 14, which is formed of hard metal or other rigid material, extends to its proximal end in an uninterrupted uniform configuration to its connection to the needle fitting 16. The connection of the insertion needle 14 to the needle fitting 16 is not shown in detail herein inasmuch as any manner of such connection is usable within the present invention as long as the interior of the insertion needle 14 is in fluid communication with the interior of the needle fitting 16. Provided stretched tightly over the insertion needle 14 is the catheter 12 itself. The catheter 12 is formed of a silicone elastomer, or other highly flexible and biologically inert material. The catheter 12 is formed so that its inner diameter in its unstretched state is approximately equal to or smaller than the inner diameter of the interior of the insertion needle 14. However, as can be seen in FIG. 2, when the catheter 12 is received over the needle 14 the catheter 12 is stretched so that its inner diameter fits tightly about the outer diameter of the insertion needle 14. At its distal end the catheter 12 is provided with a tapered end 24 adjacent to the insertion point 22 of the insertion needle 14. At its proximal end the catheter 12 is stretched over a sleeve 26 and is fixedly secured thereto. The sleeve 26 is a relatively semi-rigid tubular member formed of Teflon, polyethylene, polypropylene, or other relatively rigid and biologically inert material. The sleeve 26 is formed so that its inner diameter is just slightly greater than the outer diameter of the insertion needle 14 so that it may be slidably received thereover. As stated the proximal end of the catheter 12 has its inner surface stretched over and fixedly adhered to, as by gluing, to the exterior of the sleeve 26. The leading or distal end of the sleeve 26 ends in an abrupt edge with the edge being at a right angle relative to the longitudinal axis of both the insertion needle 14 and the catheter 12. At its proximal or trailing end the sleeve 26 is fixedly secured to the hub member 18. The hub member 18 is formed of a relatively rigid material, and is a relatively large tubular member also slidably received over the exterior of the insertion needle 14. The hub member 18 may be provided with any manner of exterior shape as may be suitable for manipulation by the human hand. As stated previously, behind the hub member 18 is the needle fitting 16, which is fixedly secured to the insertion needle 14, in contrast with the hub member 18 which is freely slidable over the insertion needle 14. The hub member 18 and the needle fitting 16 may be provided with interfitting surfaces so that they may be snugly press-fit together, if desired.

Figure 3:
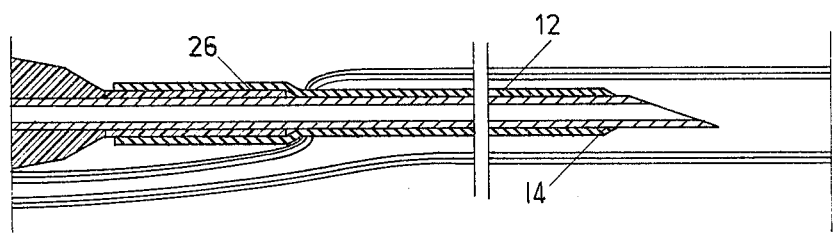
FIG. 3 is a partial cross-sectional view taken along the longitudinal center line of the device of FIG. 1, similar to FIG. 2, showing the first step in insertion of the catheter into a blood vessel.
Figure 4:
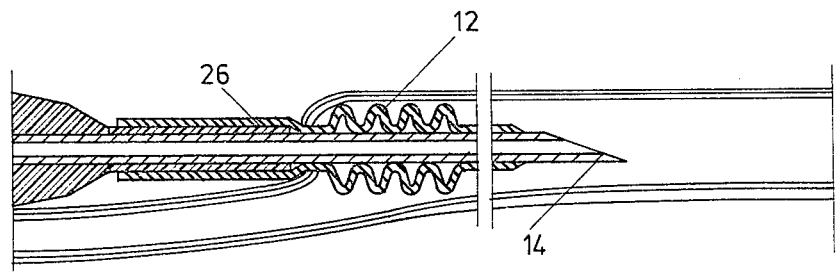
FIG. 4 is a cross-sectional view, similar to FIG. 3, showing a second step in the insertion of the catheter into the blood vessel.
Figure 5:
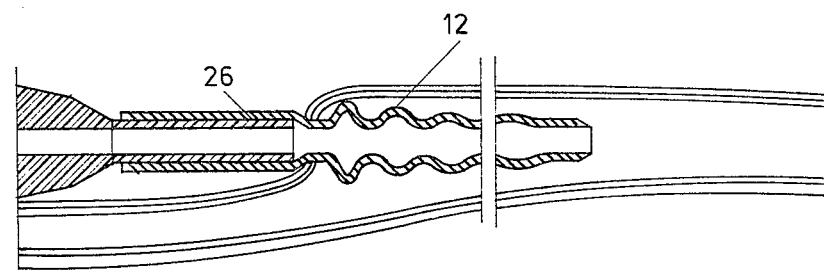
FIG. 5 is a cross-sectional view, similar to FIG. 3, showing a third step in the insertion of the catheter into the blood vessel.

Referring to FIGS. 3-5 the method of inserting and operating the catheter insertion device of FIGS. 1 and 2 will now be described. First, as is conventional in inserting a catheter into a patient, a suitable blood vessel, usually a vein, is selected. Then the insertion needle 14 is inserted into the vein, carrying the catheter 12 therewith. The tapered front end 24 of the catheter 12 helps to ensure that the catheter 12 does not bunch up at its front or distal end as the catheter 12 and needle 14 are inserted into the patient. As can be seen in FIG. 3, the bulk of the length of the insertion needle 14 is inserted into the vein of the patient, carrying the catheter 12 therewith, until the portion of the catheter 12 over the distal end of the sleeve 26 is approximately at, or just beneath, the surface of the skin of the patient. The operator inserting the catheter 12 into the patient then grasps with one hand the catheter hub 18, while he or she slowly withdraws the needle fitting 16 with the other hand. As the needle fitting 16 is withdrawn, it pulls the insertion needle 14 back therewith, which tends to drag the catheter 12 back toward its proximal end. However, because the catheter hub 18 is being held firmly in place, and because of the relative rigidity of the sleeve 26, the sleeve 26 tends to stay in position, and the catheter 12, which is attached to the sleeve 26, begins to fold in accordion-like fashion beginning just in front of the sleeve 26 as can be seen in FIG. 4. Inasmuch as the distal end of the sleeve 26 has been positioned just at or just below the skin surface of the patient, this accordion-like folding of the catheter on the insertion needle 14 as the needle is removed takes place entirely within the vein of the patient. Shown in FIG. 4 is the catheter 12 folding upon the insertion needle 14 as the insertion needle 14 is slowly withdrawn from the vein. When the insertion needle 14 is entirely withdrawn from the patient, the catheter 12 is released from the binding action of its adherence to the exterior of the insertion needle 14, and it unfolds within the vein of the patient, as is shown in FIG. 5. The normal blood flow of the patient will then stretch out the catheter 12 to its full length entirely received within the vein of the patient.

The catheter insertion device of FIGS. 1-5 offers several significant advantages over any prior art devices. In the prior art, it has generally been conventional to use Teflon or other similar semi-rigid type materials for use in infusion catheters. Such materials suffer from a significant disadvantage in that the blood tends to deposit fibrin upon the catheter within the vein with the result that a clot or a coaglum builds up in the vein which eventually closes the end of the catheter recieved within the patient. It has been experimentally determined by the applicant that a catheter formed of a silicone elastomer does not give rise to the formation of any fibrin deposits when the catheter is deposited within the vein of a patient. It is often, however, difficult to insert such a highly flexible catheter into the vein of a patient, and thus the device and method of FIGS. 1-5 is of a significant advantage in allowing such a highly flexible catheter to be inserted into a patient in a relatively quick, easy and efficient manner.

It is also an advantage of the present invention that the catheter 12 as used in the apparatus of FIGS. 1 and 2 may be of such a small diameter that its interior diameter is the same as or less than that of the needle 14 which is used to insert the catheter 12 into the patient. This is possible in view of the highly flexible nature of the silicone elastomer used for the catheter 12, and the fact that the catheter 12 can be stretched so that it may be mounted over the insertion needle 14. The catheter 12 is so stretched so that it may be inserted over the needle 14 by being soaked in freon, chloroform, or other solvent which acts to expand a silicone elastomer. The silicone elastomer catheter 12, so expanded, may then be positioned over the insertion needle 14, and then the catheter 12 may be exposed to fresh air to dry. As the solvent evaporates from the silicone catheter 12, the catheter 12 contracts into its normal state stretched tightly over the exterior of the insertion needle 14. Once the catheter 12 is removed from the needle 14 and inserted into the vein of the patient, it contracts to its undeformed size and state, thereby providing the least possible intrusion into the patient and the least amount of pain and discomfort to the patient during the infusion operation.

Two significant features of the infusion catheter insertion device 10 as shown in FIG. 2 are of a key advantage in insuring the swift and efficient operation of the insertion apparatus. The tapered end 24 of the catheter 12 is provided so as to insure that the catheter 12 does not begin to bunch at its forwardmost end as the insertion needle 14 is inserted into the patient. Inasmuch as it is desired that when the insertion needle 14 is withdrawn from the catheter 12 that the catheter 12 begin to bunch up, or fold into its accordion-like folds, from its proximal end, i.e. that adjacent to the sleeve 26, it is desired that no folding at the forwardmost end of the catheter 12 be experienced when the catheter 12 is inserted into the skin. The tapered end 24 is provided to insure that the catheter, while on the insertion needle 14, slides smoothly into the incision into the skin made by the insertion point 22 of the insertion needle 14 without bunching up as it travels therethrough. In order to further insure that the accordion-like folds of the catheter 12 are formed at the desired location, the distal end of the sleeve 26 is provided with its abrupt edge. This abrupt edge, in conjunction with the stretched state of the catheter 12, ensures that the catheter 12 will begin to fold from its rearmost end just in front of the sleeve 26 as the insertion needle 14 is withdrawn from the catheter 12. Thus it is of great importance that the sleeve 26 be of a relatively rigid material so that it will retain its shape in helping to force the catheter 12 to remain within the patient's vein as the insertion needle 14 is withdrawn therefrom.

After the insertion needle 14 is withdrawn from the patient, the catheter 12 may be used in a similar manner to conventional catheters. Any conventional fitting of any of the types widely known in the art may be attached to the catheter hub member 18 so as to infuse the desired material through the catheter 12 into the vein of the patient. The highly flexible nature of the catheter 12 ensures that the catheter 12 will always be stretched to its fullest extent in the vein inasmuch as even the relatively gentle current of a vein will act on the highly flexible catheter 12 to stretch it out to its fullest longitudinal length. During the use of the catheter 12, the portion of the catheter 12 under which the sleeve 26 is received should be positioned near or in the incision into the skin, in an effort to ensure that a minimum of blood drips from the incision during the infusion operation.

Figure 6:
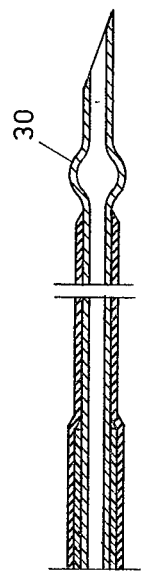
FIG. 6 is a cross-sectional view, similar to FIG. 2, taken through an alternative embodiment of a catheter insertion device constructed in accordance with the present invention.
Figure 7:
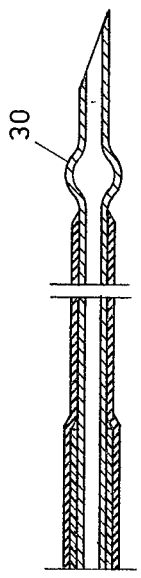
FIG. 7 is a cross-sectional view, similar to FIG. 2, taken along the longitudinal center line of yet another alternative embodiment of a catheter insertion device constructed in accordance with the present invention.

Shown in FIGS. 6 and 7 are two variations of the insertion needle 14 which are usable within the present invention. Both of these variations are intended to insure to even a greater degree that the catheter 12 does not begin to bunch or fold in its accordion-like fashion at its distal end as the insertion needle 14 is inserted into the patient. Thus in FIG. 6, the insertion needle 14 provided with a swedged portion 28, which is an enlarged portion of the insertion needle 14 formed at the forwardmost distal end 22 of the insertion needle 14. In the alternative embodiment shown in FIG. 7, the insertion needle 14 is provided with a spherical bulb 30 in it adjacent to the distal edge of the insertion needle 14. The bulb 30 is a small enlarged portion of the exterior diameter of the insertion needle 14. Behind either the swedge portion 28 or the bulb 30, the forward edge of the catheter 12 is positioned, with the catheter 12 preferably still having the forward tapered end 24, although the tapered end 24 may optionally be omitted if either of the swedged portion 28 or the bulb 30 is utilized. Either the swedged portion 28 or the bulb 30 functions to insure that the forward edge of the catheter 12 is not engaged by the skin when the distal end of the insertion needle 14 is inserted through the skin into the patient. This is to ensure that when the catheter 12 begins to fold in the accordion-like manner, that it folds from its rearmost, rather than its foremost, end.

It is understood that the present invention is not limited to the particular construction and arrangement of parts illustrated and disclosed herein, but embraces all such modified forms thereof as come within the scope of the following claims.

I claim:
1. A catheter insertion device comprising:
an elongated hollow needle (14) sharpened at its distal end (22);
a flexible catheter (12) formed of a silicon elastomer and positioned stretched over the needle (14);
a hub member (18) slidably received over the proximal end of the needle (14); and
a semi-rigid sleeve (26) extending from the hub member (18) toward the distal end of the needle (14) and slidably received around the needle (14), the proximal end of the catheter (12) being stretched over the sleeve (26), the sleeve (26) serving to force the catheter (12) off of the needle (14) as the needle (14) is withdrawn through the hub member (18).
2. A catheter insertion device as claimed in claim 1 wherein an elongated portion (28 or 30) is formed adjacent the distal end of the needle (14) to aid in insertion of the catheter (12) into the patient without bunching.
3. A catheter insertion device as claimed in claim 2 wherein the enlarged portion is formed as a swedged portion (28) at the extreme distal end of the needle (12).
4. A catheter insertion device as claimed in claim 2 wherein the enlarged portion is formed as a spherical bulb (30) located near the distal end of the needle (12).
5. A catheter insertion device as claimed in claim 1 wherein the catheter (12) is tapered at its distal end (24) to aid in its insertion into the patient.
6. A catheter insertion device as claimed in claim 1 wherein the sleeve (26) has an abrupt edge at its distal end to aid in forcing the catheter (12) off of the needle (14).
7. A catheter insertion device as claimed in claim 1 wherein the catheter (12) in its unstretched state is no larger in diameter than the needle (14).

* * * * *